United States Patent

Paltieli

[11] Patent Number: 5,807,264
[45] Date of Patent: Sep. 15, 1998

[54] ENDOSCOPE APPARATUS AND METHOD FOR DETECTING CILIA MOTION USING MULTIMODE DETECTION FIBERS TO COLLECT BACK-SCATTERED LIGHT

[76] Inventor: Yoav Paltieli, 51 Einstein Street, Haifa 34602, Israel

[21] Appl. No.: 632,334

[22] Filed: Apr. 10, 1996

[30] Foreign Application Priority Data

Apr. 11, 1995 [IL] Israel ........................................ 113333

[51] Int. Cl.⁶ ........................................................ A61B 5/11
[52] U.S. Cl. ........................... 600/477; 600/478; 600/595
[58] Field of Search ....................... 600/101, 109, 600/117, 138, 139, 181, 310, 342, 476–478, 587, 595; 128/664–666, 633, 634, 774, 782; 385/116, 117; 356/39, 40

[56] References Cited

U.S. PATENT DOCUMENTS

| | | |
|---|---|---|
| 3,430,047 | 2/1969 | Hurkamp . |
| 3,655,259 | 4/1972 | Miyauchi et al. . |
| 4,128,760 | 12/1978 | Del Signore, II . |
| 4,210,029 | 7/1980 | Porter ................................. 128/634 X |
| 4,213,462 | 7/1980 | Sato . |
| 4,349,255 | 9/1982 | Takayama . |
| 4,423,436 | 12/1983 | Kimura . |
| 4,476,875 | 10/1984 | Nilsson et al. ........................... 128/666 |
| 4,479,499 | 10/1984 | Alfano .................................... 128/665 |
| 4,535,758 | 8/1985 | Longacre, Jr. . |
| 4,588,294 | 5/1986 | Siegmund . |
| 4,598,715 | 7/1986 | Mächler et al. ......................... 128/634 |
| 4,737,142 | 4/1988 | Heckele . |
| 4,743,107 | 5/1988 | Aizu et al. ........................... 128/691 X |
| 4,746,211 | 5/1988 | Ruth et al. ........................... 128/691 X |
| 4,785,814 | 11/1988 | Kane ....................................... 128/634 |
| 4,913,142 | 4/1990 | Kittrell et al. ......................... 606/15 X |
| 4,938,205 | 7/1990 | Nudelman . |
| 4,963,960 | 10/1990 | Takami . |
| 4,969,034 | 11/1990 | Salvati . |
| 5,159,920 | 11/1992 | Condon et al. . |
| 5,579,774 | 12/1996 | Miller et al. ......................... 128/672 X |

OTHER PUBLICATIONS

Conceptus, Inc. Soft Torque Catheter, San Carlos, CA (Product Brochure).

Lee WI, Verdugo P. Laser Scattering Spectroscopy: A New Application in the Study of Ciliary Activity. Biophys J 1976; 1115–9.

*Primary Examiner*—John P. Leubecker
*Attorney, Agent, or Firm*—Helfgott & Karas, P.C.

[57] ABSTRACT

An endoscope apparatus for detecting cilia motion while examining the interior of a body. The endoscope apparatus including a long slender tube having a probe tip at one end, which is inserted into the body to be examined. First, second and third optical fibers extend through the tube to the probe tip. A source of light at the opposite end of the tube aligned with the first optical fiber for transmitting light into the body via the probe tip. Light detectors are at the opposite end of the tube, one in alignment with each of the second and third optical fibers, for receiving light transmitted therethrough back-scattered from the interior of the body. A differential measuring element for differentially measuring the outputs of the two detectors such as to substantially cancel out artifacts and to increase the signal-to-noise ratio. The differential measuring element operates in a frequency range of 0.5–30 Hz in order to detect the range of frequencies of typical cilia beats.

10 Claims, 4 Drawing Sheets

PARAMETERS:

TOTAL_AV_TIME =0.60  NCALC = 11

N_POINTS =  128  TIME =  18:9:22

MAX_FREQ= 20.00  DATE =19-4-1990

FILE_REC =5

SAMP_REC =5

ENDOSCOPE APPARATUS AND METHOD FOR DETECTING CILIA MOTION USING MULTIMODE DETECTION FIBERS TO COLLECT BACK-SCATTERED LIGHT

The present invention relates to endoscopes for examining the interior of a body, and particularly to endoscopes of the optical-fiber type.

The invention is particularly useful for the real-time, in vivo measurements of the ciliary beat frequency (CBF) of the human fallopian tube during laparotomy or laparoscopy. The invention is therefore described below with respect to such application, but it will be appreciated, as will also be indicated below, that the invention could advantageously be used in other applications as well, particularly in the ENT (ear, nose, throat) field.

Cilia are tiny hairlike appendages, about 0.25 $\mu$m in diameter, that are built from bundles of parallel microtubules. They extend from many kinds of epithelial cells and are found in most animal species and in some lower plants. Their primary function is to move fluid over the surface of cells, or to propel cells through fluid. Impairment of ciliary activity in animals may produce infertility by interference with ovum pickup by the fimbria and transport through the fallopian tubes. For this reason, evaulation of the ciliary beating can serve as a viable tool for medical evaluation and treatment of infertile women.

Also, the mucociliary system is one of the most important airway defense mechanisms, and knowledge of the ciliary beat frequency is important in understanding this system. Drugs, allergies, and upper respiratory infections are known to affect the ciliary mobility.

A number of techniques have been described in the literature for measurement and evaluation of CBF. One known technique is based on the detection of back-scatted light (from ciliary epithels) and is described in Lee WI, Verdugo P. Laser Scattering Spectroscopy: A New Application in the Study of Ciliary Activity. Biophys J 1976; 16:1115-9. However, one of the problems in real-time measurement of ciliary motion, particularly when using a back-scattered light technique, is the spurious low frequency signals originating from breathing and heartbeat movements of the patient and hand movements of the surgeon. These artifacts substantially reduce the signal-to-noise ratio.

An object of the present invention is to provide an improved endoscope for examining the interior of a body based on the detection of light back-scattered from the interior of the body being examined. Another object of the present invention is to provide an improved endoscope particularly useful in measuring and evaluating CBF in a real-time manner, but which may be used in other applications.

According to the present invention, there is provided an endoscope for examining the interior of a body, comprising: a long slender tube having a probe tip at one end insertable into the body to be examined; first, second and third optical fibers extending through the tube to the probe tip; a source of light at the opposite end of the tube aligned with the first optical fiber for transmitting light into the body via the probe tip; light detectors at the opposite end of the tube, one in alignment with each of the second and third optical fibers, for receiving light transmitted therethrough back-scattered from the interior of the body; and differential measuring means for differentially measuring the outputs of the two detectors such as to substantially cancel out artifacts and to increase the signal-to-noise ratio.

According to further features in the preferred embodiment of the invention described below, the first optical fiber has a small optical core such that it operates as a single mode fiber; the second and third optical fibers have larger optical cores than the first optical fiber and operate as multi-mode fibers.

An endoscope constructed in accordance with the foregoing features has been found to substantially reduce the motion artifacts due to breathing and heartbeat movements of the patient and hand movements of the surgeon. By using two collecting optical fibers, the motion artifacts tend to affect both optical fibers in the same manner, and thus may be cancelled out by the differential treatment of the measurements; on the other hand, fluctuations resulting from ciliary motion detected in two different coherence areas produce uncorrelated fluctuating signals and thereby tend to increase the signal. In addition, the use of a single-mode fiber of very small core diameter produces a light intensity profile close to a smooth Gaussian profile, independent of fiber flexing, and thereby tends to avoid speckle pattern fluctuations due to fiber movements. The low coherence of the back-scattered light is not significantly affected by the flexing of the multimode fibers.

Further features and advantages of the invention will be apparent from the description below.

The invention is herein described, by way of example only, with reference to the accompanying drawings, wherein.

Figure 1:
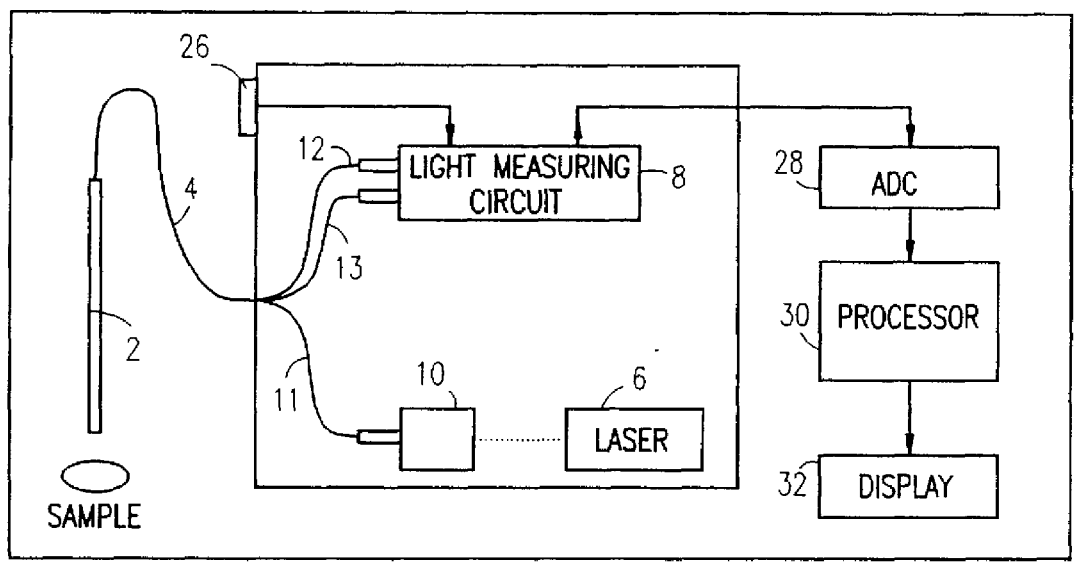
FIG. 1 is a block diagram illustrating one form of endoscope apparatus constructed in accordance with the present invention for examining the interior of a body.
Figure 3:
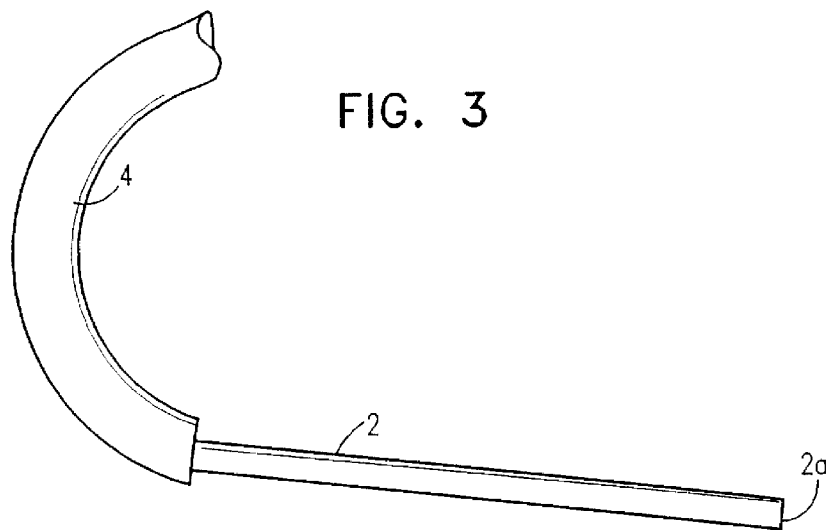
Figure 4:
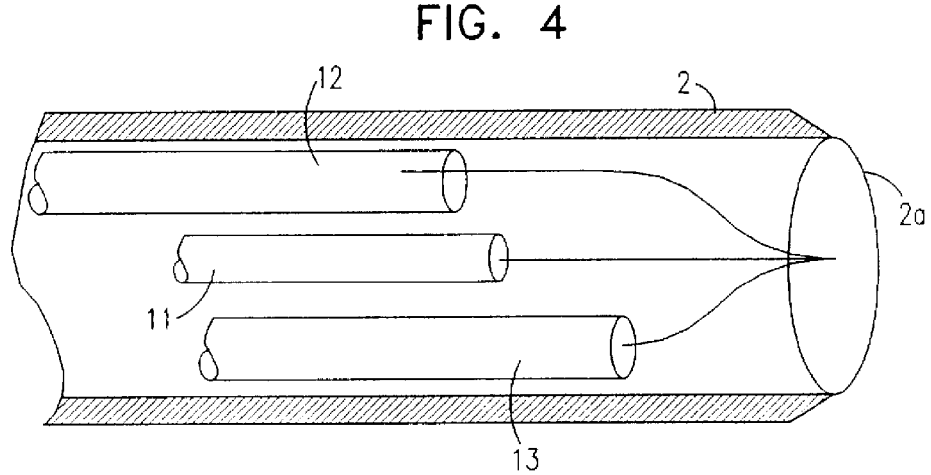
Figure 5:
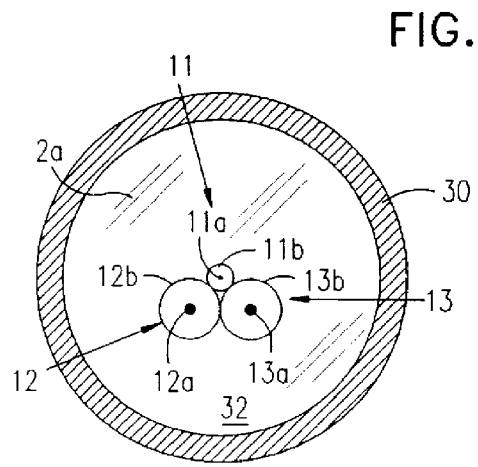
Figure 6:
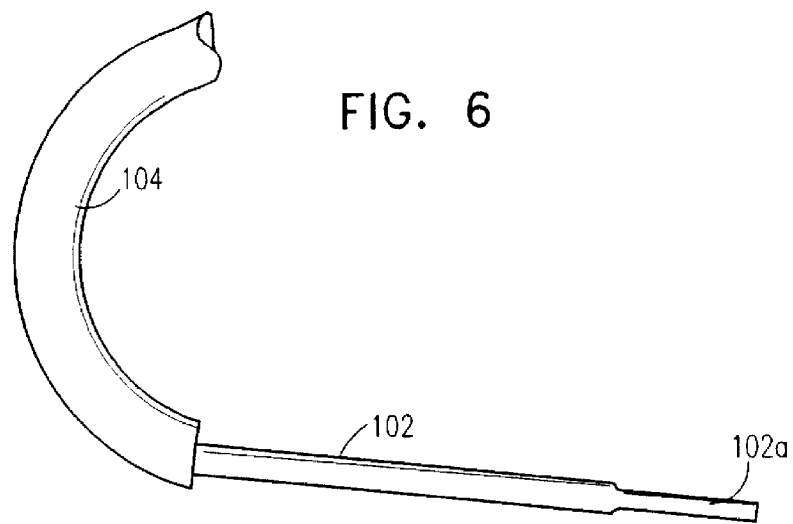
Figure 7:
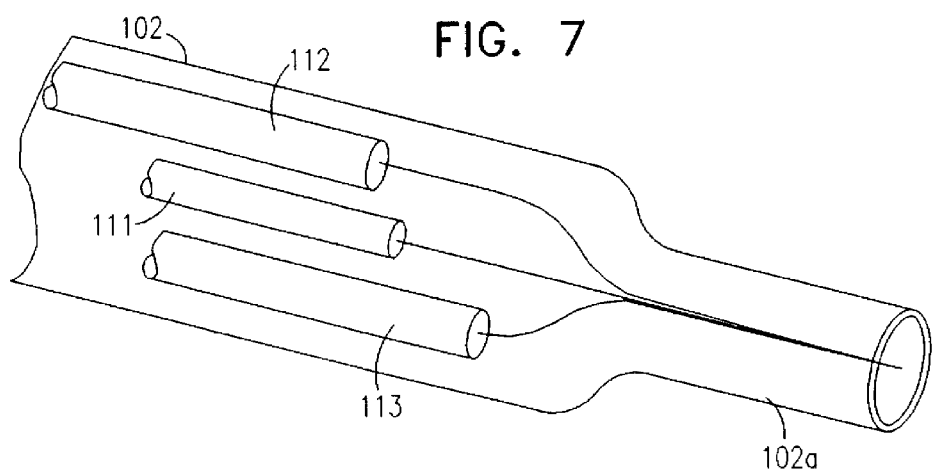
Figure 8:
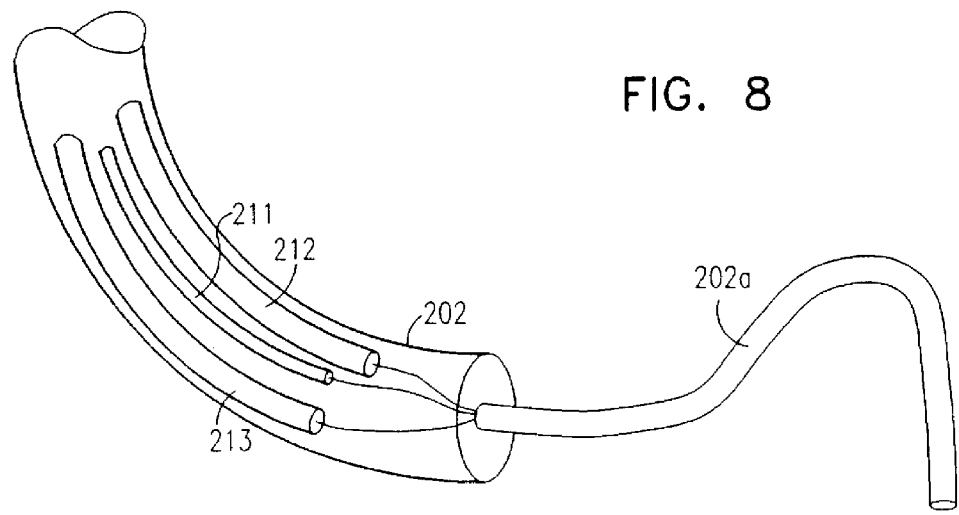
Figure 9:
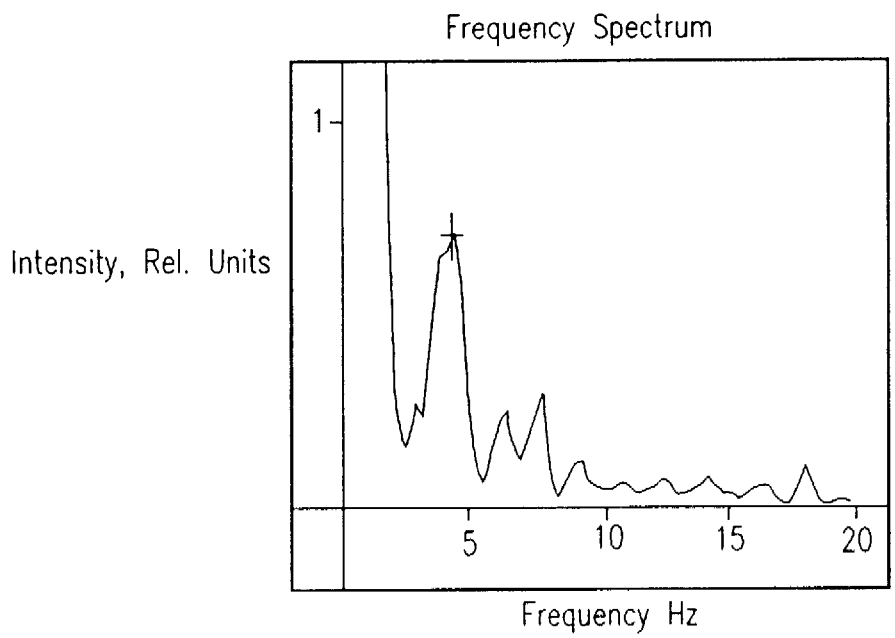

FIG. 3 more particularly illustrates the endoscopic probe in the apparatus of FIG. 1;

FIG. 4 more particularly illustrates the probe tip in the endoscope of FIG. 3;

FIG. 5 is an enlarged sectional view more particularly illustrating the end face of the probe tip in the endoscope of FIGS. 3 and 4;

FIG. 6 illustrates an endoscope particularly useful for measuring CBF in the middle ear;

FIG. 7 is an enlarged fragmentary view more particularly illustrating the probe tip in the endoscope of FIG. 6;

FIG. 8 illustrates an endoscope particularly useful for measuring CBF in the breathing tracts; and FIG. 9 illustrates a sample of a display produced as a result of CBF measurements using the apparatus of FIG. 1.

The apparatus illustrated in the drawings is particularly useful for measuring CBF (ciliary beat frequency) in laparoscopy or laparotomy (FIGS. 2 and 3), or in the middle ear (FIGS. 6 and 7) or in the breathing tracts (FIG. 8).

As shown in FIG. 1, the apparatus includes an endoscope in the form of a long, slender, rigid tube 2 insertable at one end into the body to be examined. The opposite end of the rigid tube 2 is connected via a flexible sleeve 4 to a source of light 6 for illuminating the interior of the body to be examined, and a light measuring circuit 8 for measuring the back-scattered light from the interior of the examined body.

The source of light 6 is a laser. It is coupled via a fiber coupler 10 to the end of a single mode fiber 11 extending via the flexible sleeve 4 into the endoscope 2 for transmitting the light from the laser to the examined body. Endoscope 2 and the flexible sleeve 4 include two further optical fibers 12, 13; these are multimode fibers and are connected to the light measuring circuit 8 for transmitting thereto the back-scattered light from the examined region.

Figure 2:
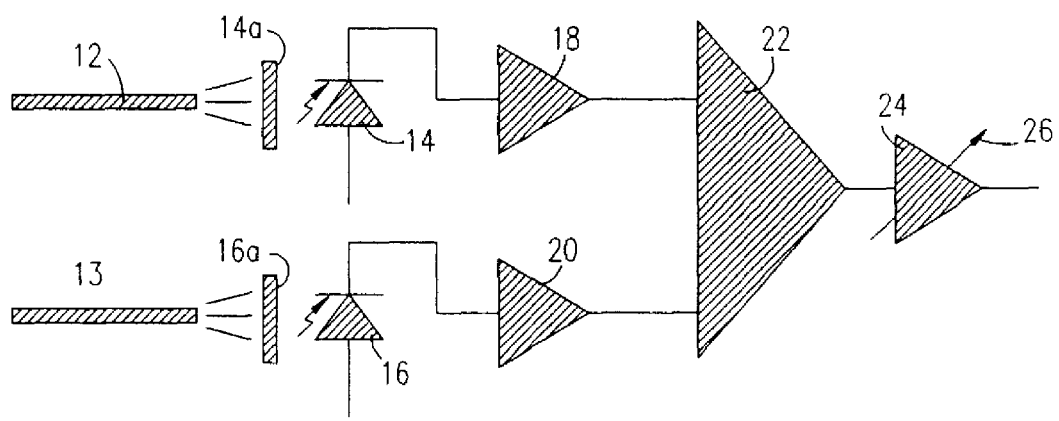
FIG. 2 is a block diagram illustrating the electrical circuit in the apparatus of FIG. 1.

The light measuring circuit 8 is more particularly illustrated in FIG. 2. It includes: two light detectors 14, 16, one for each of the two light-collecting fibers 12, 13; two preamplifiers 18, 20 for preamplifying the outputs of the two light detectors 14, 16; and a differential amplifier 22 for receiving the amplified outputs of the two light detectors. The output of differential amplifier 22 thus corresponds to the momentary difference in the amount of light received by the two light detectors 14, 16 from their respective collector fibers 12, 13.

The output from differential amplifier 22 is fed to a bandpass filter and gain control unit 24 to amplify the range of frequencies of typical cilia beats (0.5–30 Hz). The gain of unit 24 is controlled by a variable-gain potentiometer 26 (FIG. 1). As further shown in FIG. 1, the output from the light measuring circuit 8 is fed, via an analog-to-digital converter 28 to a digital processor 30 for processing and display via a display unit 32.

Laser 6 is preferably a low power 2 mW He—Ne laser, or a dye laser. It is coupled by a single-mode fiber coupler 10 to the single-mode illuminating fiber 11 leading from the flexible sleeve 4 into the endoscope 2. FIGS. 3–5 more particularly illustrate the structure of the endoscope.

Thus, as shown particularly in FIG. 5, the endoscope 2 includes a long outer rigid tube 30, preferably of stainless steel, enclosing the three optical fibers 11, 12 and 13. At the probe tip 2a, the fibers are embedded in an epoxy resin 32 whose outer face is polished. The probe tip is thus sealed to prevent air leakage and is sterilizable.

The illuminating fiber 11 is a single-mode fiber, including an inner core 11a (FIG. 5) of very small diameter, an outer cladding 11b, and an outer jacket (not shown in FIG. 5). On the other hand, the two collecting fibers 12, 13, include large-diameter cores 12a, 13a, claddings 12b, 13b, and outer jackets (not shown in FIG. 5). All three fibers, extend to the end of the rigid tube 2 constituting the probe tip insertable into the examined region, which probe tip has a flat, optically polished end face (FIG. 5). As shown in FIG. 4, the three optical fibers 11, 12, 13 are stripped of their jackets at their ends so that only their cores and claddings are exposed, and are close to each other, at the end face (FIG. 5) of the probe tip 2a.

The diameter of the core 11a of the illuminating fiber 11 is so small that it can sustain only the lowest transversal laser mode. Under these conditions, the laser intensity profile is close to a smooth Gaussian and is independent of fiber flexing. On the other hand, the cores of the two back-scattered light collecting fibers 12, 13 are of substantially larger diameter and have a relatively high numerical aperture (e.g., 0.316) so as to serve as multimode fibers. They collect a large fraction of the scattered light and transmit such light to their respective light detectors 14, 16.

Each light detector 14, 16 is preferably a photodiode and includes a narrow bandwidth filter 14a, 16a (FIG. 2) for passing only the wavelength of the laser 6, thereby eliminating the effects of surgical ambient or other extraneous white light not supplied from the laser.

As indicated earlier, utilizing two collecting optical fibers reduces the artifacts originating from breathing and heartbeat motions of the patient and hand motions of the surgeon or physician since such motions would affect both optical fibers in the same manner and thus tend to cancel out by the differential amplifier 22. On the other hand, fluctuations resulting from ciliary motion are detected by the two collector fibers in two different laser coherence areas, which are random and therefore do not cancel out. As a result, a relatively high signal-to-noise ratio is produced at the output of the differential amplifier 22.

As one example, the rigid steel tube 30 of the endoscope 2 may have an outer diameter of 5 mm and an inner diameter of 4 mm; the illuminating fiber 11 may have a core diameter of 4 microns, and a cladding diameter of 125 microns, and a jacket diameter of 250 microns; and each of the two collector fibers 12, 13 may have a core diameter of 100 microns, a cladding diameter of 200 microns, and a jacket diameter of 1,000 microns. The length of the rigid stainless steel tube 30 of the endoscope 2 may be 35 cm, and the length of the flexible sleeve 4 connecting the endoscope 2 to the laser 6 and light measuring circuit 8 may be about 1.5 M.

FIGS. 6 and 7 illustrate a modification in the construction of the endoscope, therein designated 102, particularly useful for CBF measurements in the middle ear. This construction also includes the three optical fibers 111, 112, 113, enclosed within a rigid tube 102. Here, however, the end of the tube 102 constituting the probe tip 102a is reduced in diameter, e.g., to about 1 mm, so as to facilitate its insertion through the hole in a button inserted in the ear membrane, to release fluid accumulating during ear infections common in growing children.

FIG. 8 illustrates an endoscope particularly useful for measuring CBF in the breathing tracts. This arrangement also includes the three optical fibers 211, 212, 213, as described above, except that they are enclosed in a flexible tube 202 for insertion into the breathing tract, or through the channel of a flexible endoscope 202a.

Filters 14a, 16a in front of the light detectors 14, 16 (FIG. 2) may have maximum transmission at 633 nm, thereby matching the wavelength of the He—Ne laser 6 to eliminate the effects of ambient light. Differential amplifier 22 may have a high-pass sharp frequency cutoff at 0.5 Hz to prevent saturation of the amplifiers because of slow movements.

Processor 30 may be a personal computer which samples the output signals from the analog-to-digital converter 28 according to user-specified sampling parameters, and stores the data in the computer memory in a direct memory access mode. This enables accumulating and processing the data simultaneously. User-chosen parameters would include: averaging time (in minutes), the number of sampling points N (e.g., 32, 64, 128, 256, or 512), and maximum frequency (cycles/sec.). The maximum frequency ($F_{max}$) determines the sampling rate, which is set at $2 \times F_{max}$. For each array of N sampled data points, Fourier transformation and squaring yield the power spectrum of all the frequencies up to $F_{max}$. A larger number of sampling points N gives the same overall shape of the power spectrum at higher frequency resolution, but obviously takes longer to sample and calculate, and therefore yields a slower real-time response to the operator. The averaging time determines how many separate power spectra will be averaged in the final power spectrum.

To establish the sensitivity of CBF measurements, and the effects of probe movements and proximity to the surface, experiments were first performed in vitro on human upper respiratory tract cilia obtained by nasal smear, or slices of chicken trachea immersed in medium. Photometric microscopy served as a reference method to which observations of the laser instrument were compared under well controlled conditions.

In the second stage of the study, measurements were performed on excised human oviducts which were removed during total abdominal hysterectomy, and put into tissue culture medium (Ham's F-10). CBF measurements were performed within few minutes after the tubes were removed, since a decline in CBF was observed as a function of time. It was also observed that the CBF had declined rapidly when the medium temperature decreased. The optimal results were obtained when the probe touched gently the fimbria and when the probe was inserted into the ampulla without pressing the oviductal walls.

The parameters that gave an optimum signal to noise ratio with fast response time were found to be: average time of 0.6 min, 128 sampling points, and maximum frequency of 20 Hz, giving a display of updated spectrum ever 3.2 seconds, and final frequency power spectrum averaged for 11 spectra. Nine measurements of CBF of fimbria of excised human fallopian tubes were made with these parameters. The mean ± SEM value for the CBF was 5.9±0.5 (4.7–8.4) Hz.

In the next stage of the study, CBF of intact human oviducts was measured. Measurements were done only in menstruating women undergoing laparotomy or laparoscopy. CBF measurements were performed during laparatomy in 65 cases, during laparoscopy in 13 cases, during cesarean section in 9 cases. In 49 cases of the laparotomy group, total abdominal hysterectomy was done because of uterine myoma. In 16 cases, the indication for laparotomy was ovarian tumor and ovarian cystectomy was performed. The indication for 7 laparoscopies was tubal sterilization, and for 6 laparoscopies was infertility investigation.

The mean ± SD (standard deviation) of 142 measurements of CBF in the fimbria was 5.45±1.3 Hz and in 73 measurements in the ampulla 4.95±1.7 Hz, P (probability) <0.05.

FIG. 9 illustrates the results as displayed in the computer monitor (32, FIG. 1) which was obtained during laparoscopy of one of the women examined (Case No.2), utilizing the parameters specified in FIG. 9. The obvious frequency peak around 4.7 Hz pointed by the cursor corresponds to the CBF.

The described method was also used to study the mucociliary activity in vivo of 17 patients with a deviated nasal septum, 7 patients with allergic rhinitis, and 17 healthy persons. In this study patients suffering from purulent discharge from the nose were not investigated. The healthy persons were patients examined in the outpatient clinic, without any nasal complaints.

The patient sat relaxed on an upright chair facing the examiner. No local anesthesia was given in order not to affect the ciliary activity. The probe was introduced in each nostril under visual inspection, sounding the anterior border of the inferior caudal. The optimal signals were obtained when the probe touched gently the nasal mucosa without pressing the nasal walls which may impair mechanically cilia beating. The time of each measurement ranged for 0.4–0.6 minutes.

The mean ± SE of CBF measurements in normal cases was 7.7±0.5 Hz. The mean CBF in cases with allergic rhinitis was 5.1±0.2 Hz (t=2.7 P<0.05) and in case of septum deviation 5.4±0.3 Hz (t=2.7 P<0.05).

While the invention has been described with respect to measuring CBF in laparoscopy or laparotomy, in the bronchi or trachea, or in the middle ear, it will be appreciated that the invention could be used in many other applications.

I claim:

1. Endoscope apparatus for detecting cilia motion while examining the interior of a body, comprising:

a long slender tube having a probe tip at one end insertable into the body to be examined;

first, second and third optical fibers extending through said tube to said probe tip;

a source of light at the opposite end of the tube aligned with said first optical fiber for transmitting light into the body via said probe tip;

light detectors at said opposite end of the tube, one in alignment with each of said second and third optical fibers, for receiving light transmitted therethrough back-scattered from the interior of the body, wherein said first optical fiber has a small optical core such that it operates as a single mode fiber, wherein said second and third optical fibers each have a larger optical core than said first optical fiber and each have a relatively high numerical aperture and operate as multi-mode detection fibers;

and differential measuring apparatus for differentially measuring the outputs of said two detectors in a frequency range of 0.5–30 Hz such as to substantially cancel out artifacts and to increase the signal-to-noise ratio.

2. The apparatus according to claim 1, further including a narrow-band filter located in front of each light detector to filter out light not emanating from said light source.

3. The apparatus according to claim 1, wherein said optical fibers are embedded in an epoxy resin at said probe tip.

4. The apparatus according to claim 1, said three optical fibers extend through the tube to said light source and detectors and are enclosed by a flexible sleeve.

5. The apparatus according to claim 1, wherein said tube is of stainless steel.

6. The apparatus according to claim 1, wherein said tube has an outer diameter of up to 5 mm.

7. The apparatus according to claim 1, wherein said tube is reduced in diameter at said probe tip.

8. The apparatus according to claim 1, wherein said tube is of flexible material.

9. A method for detecting cilia motion, comprising:

illuminating an interior of a body to be examined by transmitting light from a source of light with a single mode optic fiber;

using said single mode optic fiber to substantially eliminate speckle pattern fluctuations due to fiber motion;

collecting back-scattered light from said interior of said body with two multimode, relatively high numerical aperture detection optic fibers, said fibers having a larger diameter core than said single mode optic fiber;

transmitting said back-scattered light with said multimode detection fibers to light detectors; and processing a difference in an amount of said back-scattered light received by said light detectors, said difference being caused by a cilia motion, to detect said cilia motion.

10. The method according to claim 9 and comprising using said single mode optic fiber to produce a generally smooth Gaussian light intensity profile of said illuminated interior independent of flexing of any of said fibers.

* * * * *